US00PP14781P2

(12) United States Plant Patent
Fear et al.

(10) Patent No.: US PP14,781 P2
(45) Date of Patent: May 11, 2004

(54) RASPBERRY PLANT NAMED 'DRISCOLL MADONNA'

(50) Latin Name: *Rubus idaeus L.*
Varietal Denomination: Driscoll Madonna

(75) Inventors: Carlos D. Fear, Aptos, CA (US); Richard E. Harrison, Aptos, CA (US); Fred M. Cook, Aptos, CA (US); Gavin Sills, Watsonville, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 0 days.

(21) Appl. No.: 10/306,453

(22) Filed: Nov. 27, 2002

(51) Int. Cl.[7] ..... A01H 5/00
(52) U.S. Cl. ..... Plt./204
(58) Field of Search ..... Plt./204

*Primary Examiner*—Anne Marie Grunberg
*Assistant Examiner*—Susan B. McCormick
(74) *Attorney, Agent, or Firm*—Pennie & Edmonds LLP

(57) ABSTRACT

The present invention relates to a new and distinct cultivar of raspberry plant named Driscoll Madonna. The new cultivar is distinguished from other raspberry cultivars by its large fruit with excellent fruit firmness and structure. The new cultivar is distinguished from its seed parent by having better flavor. The new cultivar is distinguished from its pollen parent by producing larger, firmer fruit.

3 Drawing Sheets

Latin name of the genus and species of the plant claimed: The variety is botanically identified as *Rubus idaeus L.*

BACKGROUND OF THE INVENTION

The new cultivar of raspberry plant was developed from the hybridization of the selection of 'R652.1' (an unpatented variety) as the seed parent with the selection 'R709.1' (an unpatented variety) as the pollen parent. The parents were crossed in 1997, whereafter fruit and seed were collected to produce seedlings for field planting in Watsonville, Calif. in 1997. The new cultivar was selected from these seedlings in 1998 for its attractive and large fruit with long pedicels. The new cultivar has been asexually propagated by in vitro shoot tip culture, root sucker division and root cuttings at the Cassin Ranch in Santa Cruz county, Calif. and has been shown to maintain the desired and distinguishing characteristics after propagation over several generations.

SUMMARY OF THE INVENTION

The present invention provides a new and distinct cultivar of red raspberry plant named 'Driscoll Madonna'. The cultivar is botanically identified as *Rubus idaeus L.* The 'Driscoll Madonna' red raspberry plant produces a primocane crop which begins in early August and continues until early November. The floricane crop begins in late May and continues until mid to late July. The fruit of 'Driscoll Madonna' is notable for its consistent large size, uniform shape and long pedicels. The fruit of 'Driscoll Madonna' does not separate easily from its receptacle.

BRIEF DESCRIPTION OF THE DRAWINGS

The accompanying photographs show typical specimens of the primocane fruit, leaves and shoot of the new cultivar, in color as nearly true as it is reasonably possible to make in color illustrations of these characteristics.

DETAILED BOTANICAL DESCRIPTION

Figure 1:
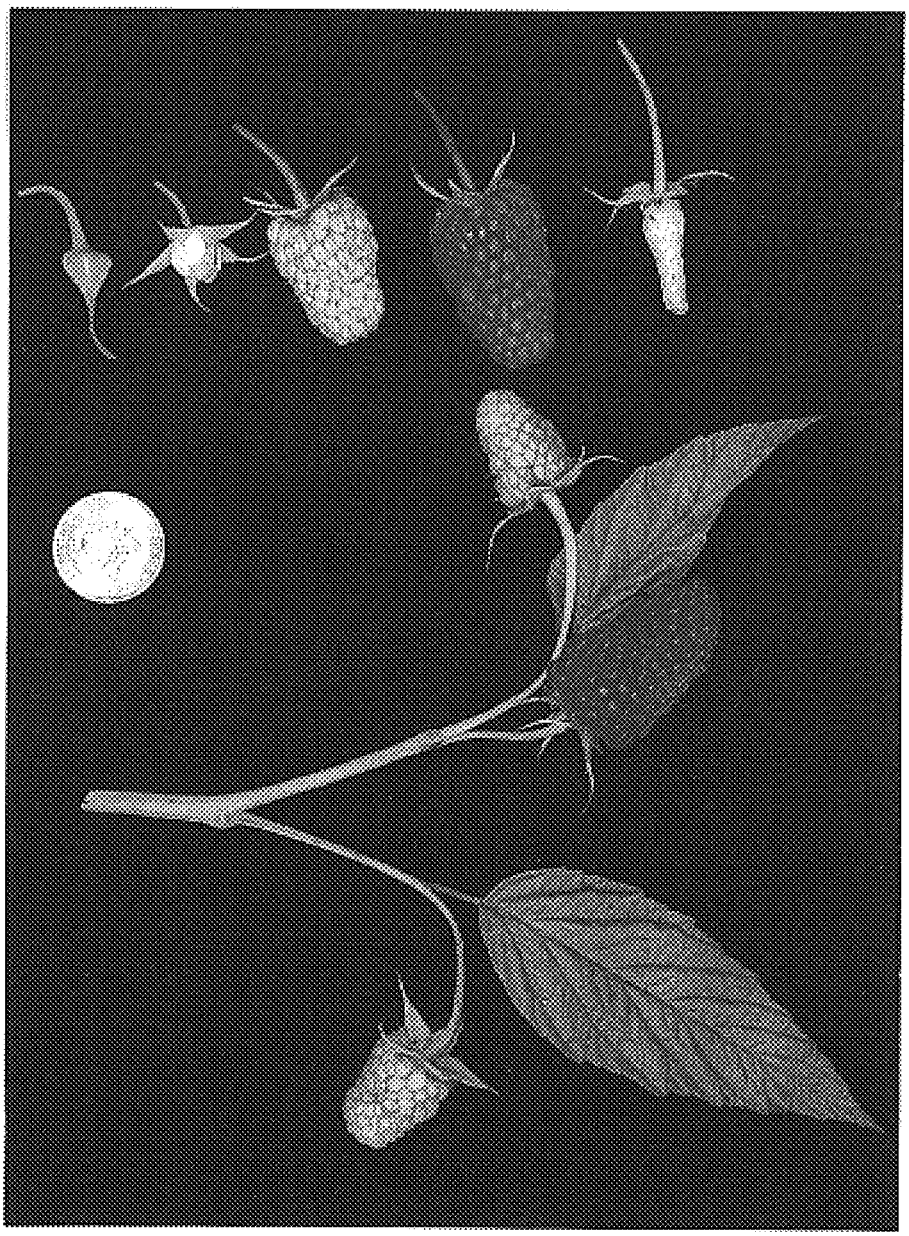
FIG. 1 is a photograph of 'Driscoll Madonna' primocane flower and fruit in various stages of development.
Figure 2:
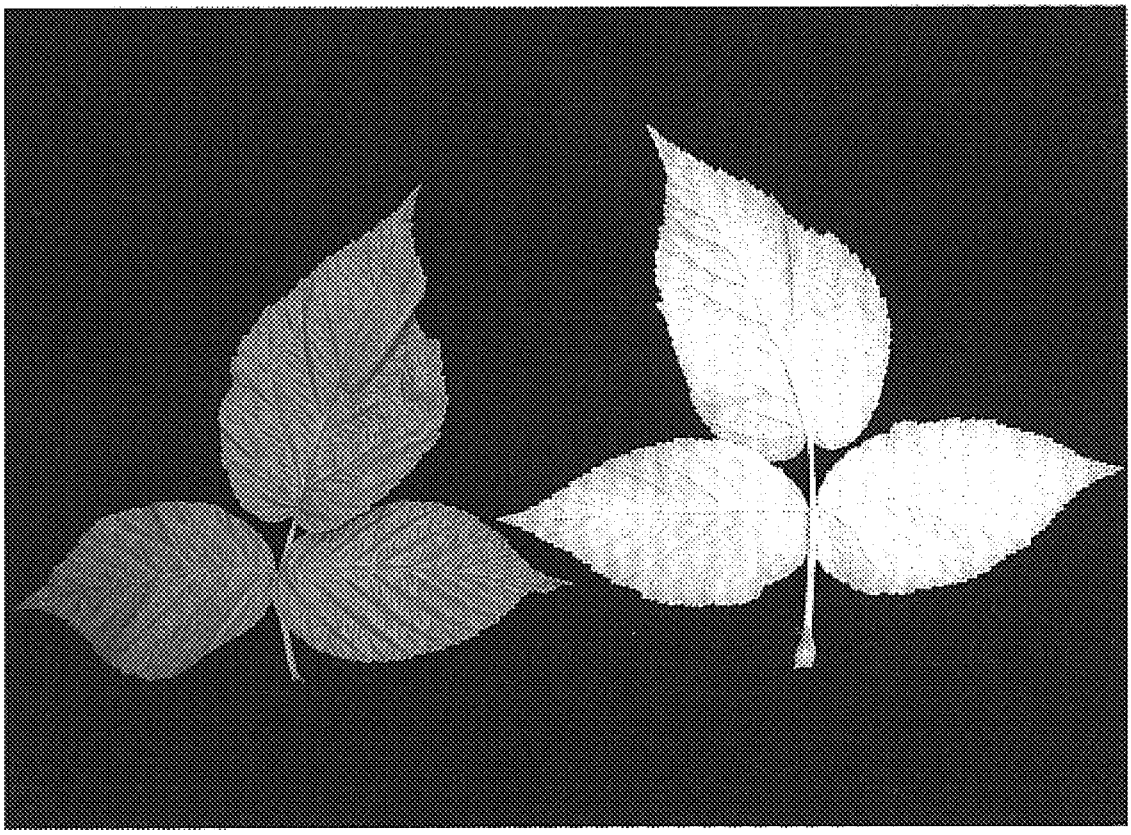
FIG. 2 is a photograph of 'Driscoll Madonna' primocane leaves showing upper and lower surfaces.
Figure 3:
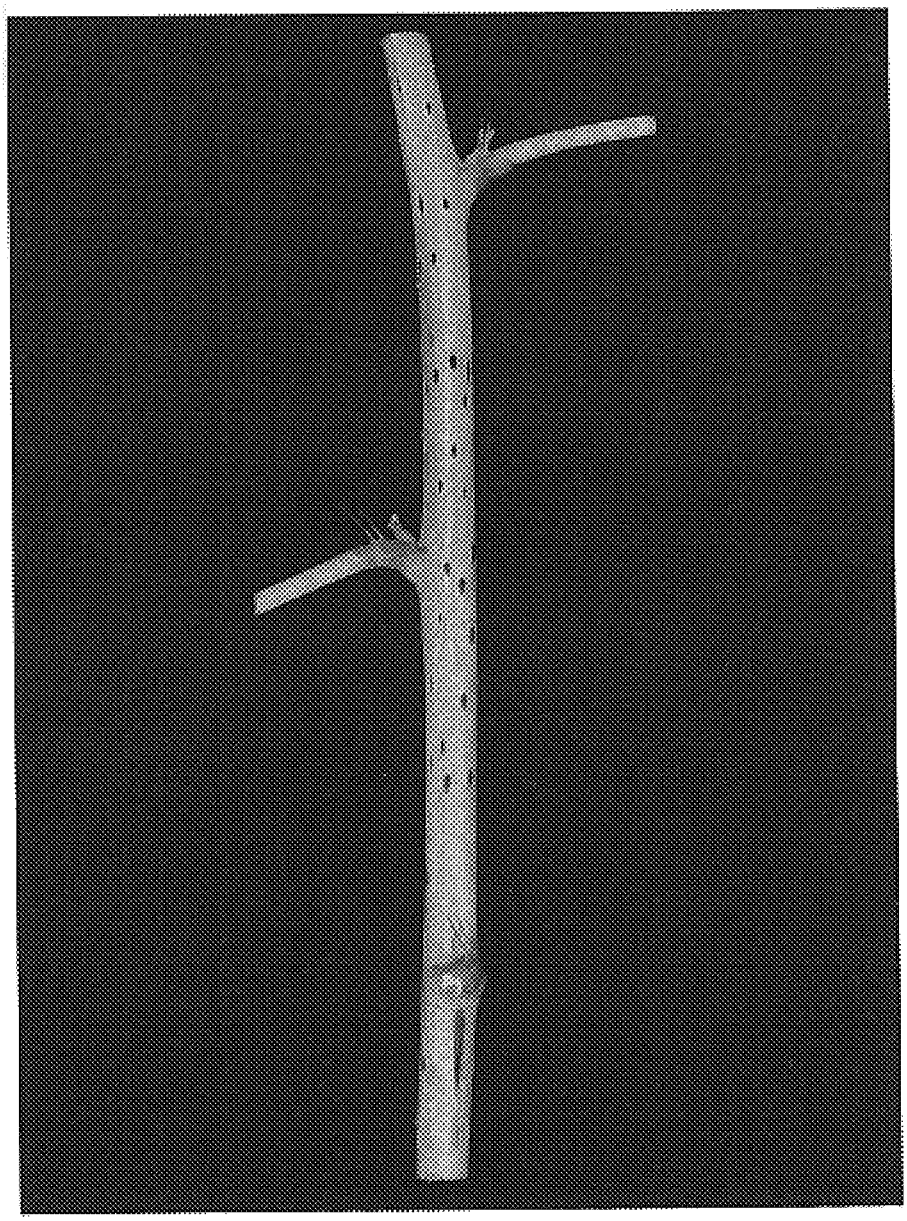
FIG. 3 is a photograph of 'Driscoll Madonna' primocane shoot.

The following detailed description of the new raspberry cultivar, 'Driscoll Madonna', is based upon observations taken of 7 to 17 month old plants and fruit grown in Watsonville, Calif. between 2001 and 2002, and is believed to apply to plants of the 'Driscoll Madonna' cultivar grown in similar conditions of soil and climate elsewhere.

Throughout this specification, color names beginning with a small letter signify that the name of the color, as used in common speech, is aptly descriptive. Color data followed by an alphanumeric code designates the color according to The R.H.S. Colour Chart published by The Royal Horticultural Society of London, England. Color designations, color descriptions, and other phenotypical descriptions may deviate from the stated values and descriptions depending upon variation in environmental, seasonal, climatic and cultural conditions.

Table 1 provides information on the plant and fruit characteristics of the new cultivar 'Driscoll Madonna' compared with characteristics of the unpatented raspberry cultivar 'Heritage'. Observations of the cultivars were taken under similar conditions.

The new variety is particularly characterized and distinguished from other cultivars by its large fruit with excellent fruit firmness and structure. The fruit is produced on long pedicels and is difficult to release from the receptacle.

The fruit color of 'Driscoll Madonna' is a bright red at harvest. Fruit of 'Driscoll Madonna' does not separate easily from the receptacle and is of good firmness at harvest. The fruit of 'Driscoll Madonna' is consistent in size and shape throughout the harvest period. The average plant height is about 240 cm and the average plant spread is about 50 cm. The pigmentation of the young shoots is 144B and there were an average of 6 young shoots in the observed plants of 'Driscoll Madonna'. The pedicel color is 144A.

The reproductive organs of 'Driscoll Madonna' are variable. The color of both surfaces of the petals is 155D and there are five petals per flower. The style color is 157D, the average number of styles per flower is about 84, the anther color is 155D, and the average number of anthers per flower is about 97. The number of petals per flower is five. The color of the seeds of 'Driscoll Madonna' is 161A, the average seed weight is about 1.2 mg, and there are an average of about 115 seeds per fruit.

The floricane yield of 'Driscoll Madonna' is high relative to the variety 'Heritage'. 'Driscoll Madonna' is distinguishable from its pollen parent, selection 'R709.1', by producing larger, firmer fruit. The new cultivar is distinguished from its seed parent, selection 'R652.1', by having better flavor.

DISEASE AND STRESS RESISTANCE

Cold tolerance of the new cultivar has not been established. Post harvest fruit rot resistance is good in comparison over many selections and varieties.

TABLE 1

PLANT CHARACTERISTICS OF 'DRISCOLL MADONNA'

| | Driscoll Madonna | Heritage |
|---|---|---|
| General | | |
| Plant size | Large | Large |
| Growth habit | Semi-erect | Erect |
| Productivity | High | Medium |
| Self-fruitfulness | Self-fruitful | Self-fruitful |
| Time of bud burst | Late | Late |
| Primocane fruiting | | |
| Percent of cane length flowering as primocane | 5-30 | 20-40 |
| Percent of total yield | 44 | 53 |
| Primocanes | | |
| Number of young shoots | Medium | Medium |
| Young shoot pigmentation | Medium | Medium |
| Length (cm) | 232 | 196 |
| Time of shoot emergence | Late | Very late |
| Glaucosity (waxy bloom) | Weak | Weak |
| Strength | Medium | Medium |
| Cane Cross section from mid cane of primocane) | Rounded to angular | Rounded |
| Dormant cane color | tan w/slight purple | brown to purple brown |
| Prickles | | |
| Pigmentation | purple | green-brownish to green |
| Density on young shoots | Medium | Dense |
| Attitude of tip | Horizontal | Downward |
| Size | Medium | Medium |
| Size: Length (base to tip at 1 m height at end of season) (mm) | 1 | 2.3 |
| Texture | smooth | Rigid |
| Presence and distribution on petioles | Present irregularly distributed | Present irregularly distribtuted |
| Pubescence on canes | Absent | Absent |
| Internodal distance (cm) (at central ⅓ of cane) | 6.0 | 5.3 |
| LEAVES | | |
| Color | | |
| Face | 147A | 147A |
| Underside | 148C | 148B |
| Relief between veins | Medium | Very weak |
| Glossiness | Medium | Medium |

TABLE 1-continued

PLANT CHARACTERISTICS OF 'DRISCOLL MADONNA'

| | Driscoll Madonna | Heritage |
|---|---|---|
| Petiole length (cm) | 6.2 | 7.7 |
| Stipule orientation | Erect | Erect |
| Arrangement | Compound | Compound |
| Number of leaflets | Usually 5 | Sometimes 3, sometimes 5 |
| Overlapping of lateral leaflets | Overlapping | Free to touching |
| Lateral leaflet: length of stalket (lower pair) | Medium | Very short |
| Terminal leaflet | | |
| Length (cm) | 11.9 | 14.6 |
| Width (cm) | 8.4 | 7.8 |
| Shape | Ovate | Ovate |
| Tip | Acuminate | Acuminate |
| Base | Round to cordate | Acute to rounded |
| Margin | Doubly serrate | Doubly serrate |
| Lateral leaflets (basal pair) | | |
| Length (cm) | 10.9 | 14.7 |
| Width | 8.1 | 8.6 |
| Orientation | Opposite | Opposite |
| Shape | Ovate | Ovate |
| Tip | Acuminate | Acuminate |
| Base | Round | Oblique |
| Rachis length between terminal leaflet and adjacent lateral leaflets (cm) | 3.8 | 1.5 |
| Margin | Doubly serrate | Doubly serrate |
| FLOWERS | | |
| Flowering period | | |
| Primocane | 14 weeks, Late June–late September | 19 weeks, Late May–late September |
| Floricane | 9 weeks, Early April–mid June | 10 weeks, Late March–mid June |
| Flower diameter (cm) | 1.4 | 1.8 |
| Petal | | |
| Length (cm) | 0.8 | 0.8 |
| Width (cm) | 0.4 | 0.3 |
| Pedicel coloration | Present, medium intensity | Present, strong intensity |
| FRUIT | | |
| Harvest season | | |
| Primocane | Mid August–late Oct | Early July–early November |
| Floricane | Late May–mid July | Late May–late July |
| Fruting lateral | | |
| Length (4th lateral from tip) (cm) | 67.8 | 49.8 |
| Number of fruit per lateral | 12.2 | 20.3 |
| Color | | |
| Immature | 46C | 42C |
| Maturing | 46A | 46A |
| Mature fruit | 59A | 59A |
| Glossiness | Medium | Medium |
| Shape | Ovate-elliptic | Ovate |
| Dimensions | | |
| Size | Large | Small |
| Length (mm) | 30 | 17 |
| Width (mm) | 22 | 18 |
| Length:width ratio | 1.36 | .94 |
| Weight (g/fruit) | | |
| Primocane | 7.5 | 3.1 |
| Floricane | 6.6 | 2.3 |
| Soluble solids (%) | 11.5 | 10.8 |

TABLE 1-continued

PLANT CHARACTERISTICS OF 'DRISCOLL MADONNA'

| | Driscoll Madonna | Heritage |
|---|---|---|
| Titratable acidity (% as citric acid) | 1.54 | 1.58 |
| Seed Weight (mg) | 2.8 | 1.5 |
| Number druplets/fruit | 115 | 72 |
| Adherence to plug | Strong | Medium |
| Firmness | Medium | Firm |
| Yield | High | Medium |

NUCLEIC ACID FINGERPRINTING

Distinctive patterns of polymorphism can be detected using a variety of nucleic acid analysis methods. In one non-limiting example, molecular genetic maps can be produced using random amplified polymorphic DNA (RAPD) (Williams et al., 1990, "DNA polymorphisms amplified by arbitrary primers are useful as genetic markers", Nucleic Acids Res. 18(22):6531–5). Using a variety of oligonucleotide primers, alone or in combination, RAPD analysis of Driscoll Madonna and Heritage yielded DNA fragment patterns that uniquely distinguish each of these genetically distinct genotypes.

We claim:

1. A new and distinctive cultivar of raspberry plant, substantially as shown and described.

* * * * *